United States Patent
Ohta (10) Patent No.: US 9,462,937 B2
(45) Date of Patent: Oct. 11, 2016

(54) OPHTHALMIC DEVICE, AND CONTROL METHOD AND PROGRAM THEREFOR

(71) Applicant: CANON KABUSHIKI KAISHA, Tokyo (JP)

(72) Inventor: Koichi Ohta, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 103 days.

(21) Appl. No.: 14/253,700

(22) Filed: Apr. 15, 2014

(65) Prior Publication Data

US 2014/0313480 A1 Oct. 23, 2014

(30) Foreign Application Priority Data

Apr. 17, 2013 (JP) ................................ 2013-086879

(51) Int. Cl.
*A61B 3/10* (2006.01)
*A61B 3/00* (2006.01)
*A61B 3/14* (2006.01)

(52) U.S. Cl.
CPC .............. *A61B 3/0025* (2013.01); *A61B 3/10* (2013.01); *A61B 3/14* (2013.01)

(58) Field of Classification Search
CPC ............................... A61B 3/0025; A61B 3/16
USPC .................................. 351/208, 246, 221, 206
See application file for complete search history.

(56) References Cited

U.S. PATENT DOCUMENTS

| 5,500,696 | A | 3/1996 | Masuda |
| 2008/0137034 | A1 | 6/2008 | Wernick |
| 2012/0249955 | A1 | 10/2012 | Sarver |
| 2013/0162946 | A1 | 6/2013 | Dobashi |
| 2014/0028977 | A1 | 1/2014 | Umekawa |
| 2014/0028978 | A1* | 1/2014 | Sakagawa ............ A61B 3/1173 351/208 |
| 2014/0313480 | A1 | 10/2014 | Ohta |
| 2014/0313485 | A1 | 10/2014 | Umekawa |

FOREIGN PATENT DOCUMENTS

| EP | 2692283 A1 | 2/2014 |
| JP | 3244873 B2 | 1/2002 |
| JP | 2003-290146 A | 10/2003 |
| JP | 2011-136109 A | 7/2011 |
| JP | 2011-188983 A | 9/2011 |

OTHER PUBLICATIONS

RK-F2 Full Auto Ref-Keratometer;Canon USA Inc; EB-022 Rev. B.
Kohnerr et al.;'Cataract Surgery With Implantation of an Artificial Lens'; Deuisches Arztebiatt International; Dtsch Arztebl Int 2009;106(43); Kohnen ei al: e-references.

* cited by examiner

*Primary Examiner* — Hung Dang
(74) *Attorney, Agent, or Firm* — Canon USA, Inc. IP Division (57) ABSTRACT

An ophthalmic device includes an acquisition unit configured to acquire a transillumination image of a pupil of a subject eye, and a determining unit configured to determine whether or not the subject eye includes an intraocular lens, based on the acquired transillumination image.

21 Claims, 8 Drawing Sheets

OPHTHALMIC DEVICE, AND CONTROL METHOD AND PROGRAM THEREFOR

BACKGROUND OF THE INVENTION

1. Field of the Invention

The present invention relates to an ophthalmic device to measure or photograph characteristics of a subject eye, a control method for the ophthalmic device, and a program.

2. Description of the Related Art

Recently, there has been a more widespread use of intraocular lenses (IOL, also called "artificial lenses") in eyes. Eyes that have had intraocular lenses inserted in them may be known as "IOL eyes". Intraocular lenses have different characteristics from crystalline or natural lenses with regard to shape, material, whether or not optical power adjustment capabilities are possessed, and so forth. Accordingly, information regarding whether a subject eye is an IOL eye needs to be obtained by an ophthalmic device in order to examine an IOL eye accurately.

Japanese Patent No. 3244873 discloses a technology in which an examiner inputs whether or not the subject eye is an IOL eye into a device, and functions of a jog dial are switched depending on that input. This configuration enables the examiner to adjust, using the jog dial, the quantity of light of a fixation target for IOL eyes, which are generally more likely to contract. Since the examiner has to input whether or not the subject eye is an IOL eye, there has been the possibility that the examination may end in failure, due to misunderstanding or erroneous operations of the examiner. There has also been a problem that the input operation places an extra burden on the examiner, and that measurement time thereby takes longer.

Now, Japanese Patent Laid-Open No. 2003-290146 has disclosed a technology for an ophthalmic photography device, where the device determines whether or not a subject eye is an IOL eye from the colour of a flare, and switches the focusing method. This configuration allows precise focusing to be performed with IOL eyes which generally more readily exhibit flares.

Further, Japanese Patent Laid-Open No. 2011-136109 has disclosed a technology for an axial length measurement device where determination is made whether or not a subject eye is an IOL eye based on reflection signals from the anterior ocular segment of the subject eye, and uses an axial length calculation method that is more suitable.

SUMMARY OF THE INVENTION

However, none of the above-described patent documents disclose using a transillumination moving image of the pupil of the subject eye when determining whether or not the subject eye includes an intraocular lens.

An ophthalmic device according to an aspect of the present invention includes an acquisition unit configured to acquire a transillumination image of a pupil of a subject eye; and a determining unit configured to determine whether or not the subject eye includes an intraocular lens, based on the acquired transillumination image.

Further features of the present invention will become apparent from the following description of exemplary embodiments with reference to the attached drawings.

DESCRIPTION OF THE EMBODIMENTS

An embodiment of the present invention will be described with reference to the drawings. Note that in the following description of the embodiment, the term "intraocular lens" will be abbreviated to "IOL", a subject eye having an intraocular lens will be referred to as "IOL eye", and a subject eye not having an intraocular lens will be referred to as "non-IOL eye". Further, an intraocular lens which is a monofocal intraocular lens will be referred to as a "monofocal IOL", an intraocular lens which is a diffractive multifocal intraocular lens will be referred to as a "diffractive multifocal IOL". Moreover, a subject eye having a monofocal intraocular lens may be referred to as a "monofocal IOL eye", and a subject eye having a diffractive multifocal intraocular lens as a "diffractive multifocal IOL eye". Note that when simply stated as "IOL eye", this includes both a subject eye having a monofocal intraocular lens and a subject eye having a diffractive multifocal intraocular lens.

Overall Configuration of the Device

Figure 1:
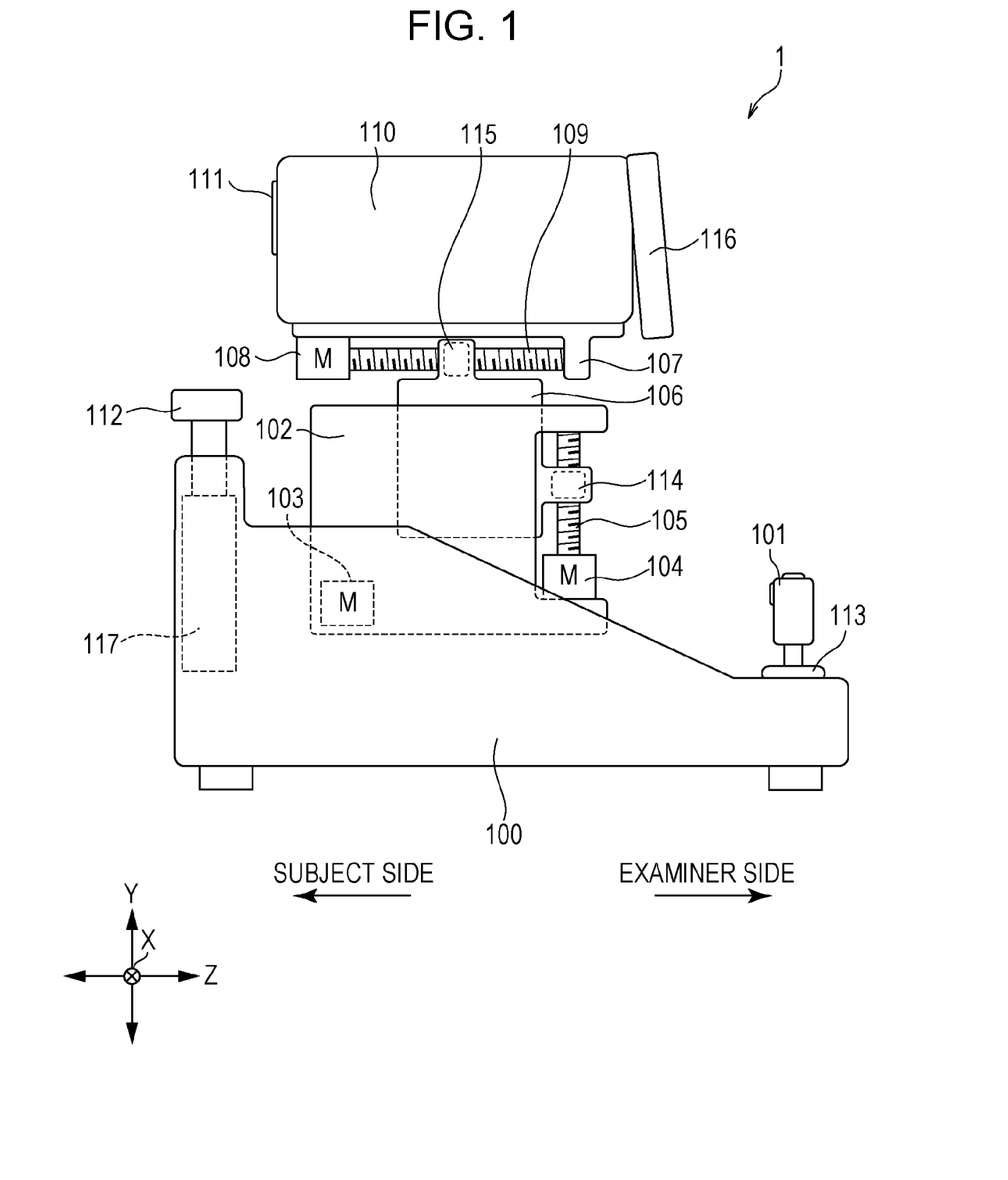
FIG. 1 is an external schematic view of an eye refractometer.

First, the device configuration of an eye refractometer 1, which is an example of an ophthalmic device related to the embodiment of the present invention, will be described with reference to FIG. 1. The eye refractometer 1 is configured to measure eye refraction as a characteristic of a subject eye E (shown in FIG. 2). Note that while the present embodiment is illustrated as an eye refractometer as an example of an ophthalmic device, the present invention can also be applied to a fundus camera or an axial length measurement device (or similar, as would be understood by the person skilled in the art) as well.

The eye refractometer 1 includes a base 100, an X-axis drive frame 102, a Y-axis drive frame 106, a Z-axis drive frame 107, and a measuring unit 110.

The X-axis drive frame 102 is movable horizontally (X-axis direction) in relation to the base 100. The X-axis direction drive mechanism of the X-axis drive frame 102 is configured including an X-axis drive motor 103, an X-axis feed screw (not illustrated), and an X-axis feed nut (not illustrated). The X-axis drive motor 103 is fixed to the base 100. The X-axis feed screw is coupled to the output shaft of the X-axis drive motor 103. The X-axis feed nut is attached to the X-axis drive frame 102, and can move in the X-axis direction by rotation of the X-axis feed screw. The X-axis feed screw rotates by the rotation of the output shaft of the X-axis drive motor 103, and the X-axis drive frame 102 moves in the X-axis direction together with the X-axis feed nut.

The Y-axis drive frame 106 is movable vertically (Y-axis direction) in relation to the X-axis drive frame 102. The Y-axis direction drive mechanism of the Y-axis drive frame 106 is configured including a Y-axis drive motor 104, a Y-axis feed screw 105, and a Y-axis feed nut 114. The Y-axis drive motor 104 is fixed to the X-axis drive frame 102. The Y-axis feed screw 105 is coupled to the output shaft of the Y-axis drive motor 104. The Y-axis feed nut 114 is attached to the Y-axis drive frame 106, and can move in the Y-axis direction by rotation of the Y-axis feed screw 105. The Y-axis feed screw 105 rotates by the rotation of the output shaft of the Y-axis drive motor 104, and the Y-axis drive frame 106 moves in the Y-axis direction together with the Y-axis feed nut 114.

The Z-axis drive frame 107 is movable longitudinally (Z-axis direction) in relation to the Y-axis drive frame 106. The Z-axis direction drive mechanism of the Z-axis drive frame 107 is configured including a Z-axis drive motor 108, a Z-axis feed screw 109, and a Z-axis feed nut 115. The Z-axis drive motor 108 is fixed to the Z-axis drive frame 107. The Z-axis feed screw 109 is coupled to the Z-axis drive motor 108. The Z-axis feed nut 115 is attached to the Y-axis drive frame 106, and can move in the Z-axis direction relative to the Z-axis feed screw 109, by rotation of the Z-axis feed screw 109. The Z-axis feed screw 109 rotates by the rotation of the output shaft of the Z-axis drive motor 108, and the Z-axis drive frame 107 moves in the Z-axis direction together with the Z-axis drive motor 108 and the Z-axis feed screw 115.

The measuring unit 110 to perform measurement is fixed to the Z-axis drive frame 107.

A light source unit 111 configured to serve as a light source (not illustrated) for alignment and to measure corneal curvature, is installed to the end of the measuring unit 110 on the subject eye side.

A joystick 101 is installed to the base 100 on the examiner side. The joystick 101 is an operation member which the examiner uses and which is configured to align the measuring unit 110 with the subject eye E. During measurement, the examiner may adjust the position of the measuring unit 110 and so forth by tilting the joystick 101.

A jog dial 113 is provided below the joystick 101. The examiner can set the distance between vertices by rotating the jog dial 113.

When measuring the eye refraction, the subject rests the chin on a chinrest 112, and rests the forehead against a forehead rest portion on the face rest frame (not illustrated) fixed to the base 100. This secures the position of the subject eye E as to the base 100.

The position of the chinrest 112 is adjustable in the Y-axis direction by a chinrest drive mechanism 117, in accordance with the size of the face of the subject.

An LCD monitor 116 serving as a display member is also installed to the end of the measuring unit 110 on the examiner side. The LCD monitor 116 can display images generated by a system control unit 401 (shown in FIG. 2) as an image generating unit; images acquired by the system control unit 401 as an acquisition unit; measurement results; and so forth. The examiner can observe the subject eye E and confirm measurement results using the LCD monitor 116.

Configuration of Optical System of Measuring Unit

Figure 2:
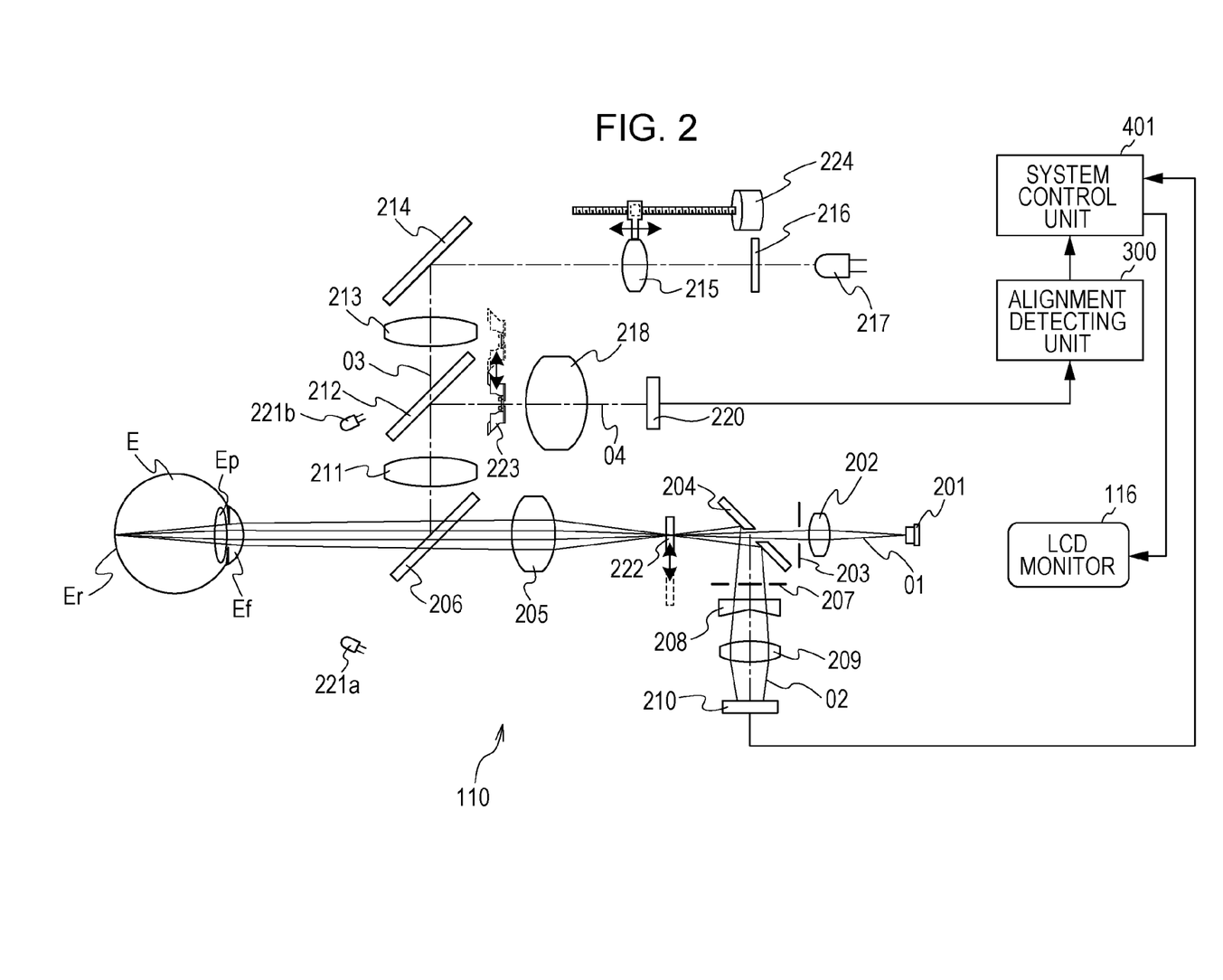
FIG. 2 is a layout view of an optical system in a measuring unit.

Next, the configuration of the optical system within the measuring unit 110 will be described with reference to FIG. 2. FIG. 2 is a layout diagram of the inside of the measuring unit 110.

The measuring unit 110 includes an optical system for measuring eye refraction, a fixation target projecting optical system, and an alignment light-receiving optical system.

The configuration of the optical system for measuring eye refraction is described next.

An eye refraction measuring light source 201 casts light having a wavelength of 880 nm. A projecting lens 202, a diaphragm 203, an apertured mirror 204, a lens 205, and a dichroic mirror 206 are arranged in this order along an optical path 01 extending from the eye refraction measuring light source 201 to the subject eye E.

The diaphragm 203 is disposed nearly or actually conjugate to a pupil Ep of the subject eye E. The dichroic mirror 206 reflects all visible light and infrared light having a wavelength of less than 880 nm from the subject eye E side, and reflects a portion of the light beam having a wavelength of at least 880 nm.

A diaphragm 207, a light beam spectroscopic prism 208, a lens 209, and an imaging device 210 are arranged in this order along an optical path 02 in the reflected direction of the apertured mirror 204. The diaphragm 207 is provided with an annular slit, and is disposed nearly or actually conjugate with the pupil Ep.

The light beam emitted by the eye refraction measuring light source 201 is focused by the diaphragm 203, and is subjected to primary imaging in front of the lens 205 by the projecting lens 202. The light beam passes through the lens 205 and the dichroic mirror 206, and is then projected into the pupil center of the subject eye E. The projected light beam is reflected by a fundus Er, and this reflected light beam (fundus reflected light beam) passes through the pupil center to again enter the lens 205. After passing through the lens 205, the reflected light beam is reflected from the apertured mirror 204.

The light beam reflected from the apertured mirror 204 is pupil-separated by the light beam spectroscopic prism 208 and the diaphragm 207, which is nearly or actually conjugate to the pupil Ep of the subject eye E, and then projected as a ring image to the light-receiving surface of the imaging device 210. The imaging device 210 converts the optical image made up of the projected light beam into signals, and outputs the signals. The system control unit 401 generates an image from the signals output from the imaging device 210.

If the subject eye E has normal vision, this ring image will form a predetermined or expected circle. For eyes with myopia, the ring image circle is smaller than that of eyes with normal vision. For eyes with hyperopia, the ring image circle is larger than that for eyes with normal vision.

For subject eyes E with astigmatism, the ring images forms an ellipse. In this case, the angle formed by the horizontal axis and the ellipse is the astigmatism axial angle. The eye refraction of the subject eye is calculated on the basis of the coefficient from this ellipse.

A fixation target projecting optical system and an alignment light-receiving optical system are arranged along the reflected direction of the dichroic mirror 206. The alignment light-receiving optical system is used for both observation of the anterior ocular segment of the subject eye E, and alignment detection.

The fixation target projecting optical system is configured as follows. A lens 211, a dichroic mirror 212, a lens 213, a reflecting mirror 214, a lens 215, a fixation target 216, and a fixation target lighting light source 217 are arranged in this order along an optical path 03 of the fixation target projecting optical system.

The fixation target lighting light source 217 lights during fixation guidance, to illuminate the fixation target 216 from the rear with a projected light beam. The light beam that has passed through the fixation target 216 is projected to the fundus Er of the subject eye E via the lens 215, the reflecting mirror 214, the lens 213, the dichroic mirror 212, and the lens 211.

The lens 215 is movable in the optical axis direction by a fixation target guidance motor 224, thereby performing diopter guidance for the subject eye E, enabling a fogging state to be achieved.

An alignment light-receiving optical system is disposed in the reflecting direction of the dichroic mirror 212. An alignment prism diaphragm 223, an imaging lens 218, and an imaging device 220 are arranged in this order along an optical path 04 of the alignment light-receiving optical system.

The alignment prism diaphragm 223 can be inserted into and removed from the optical path 04 by an alignment prism diaphragm insertion and removal solenoid 411 (omitted from illustration in FIG. 2). When the alignment prism diaphragm 223 is on the optical path 04, alignment can be performed, and when removed from the optical path 04, anterior ocular segment observation or transillumination observation can be performed.

Figure 3:
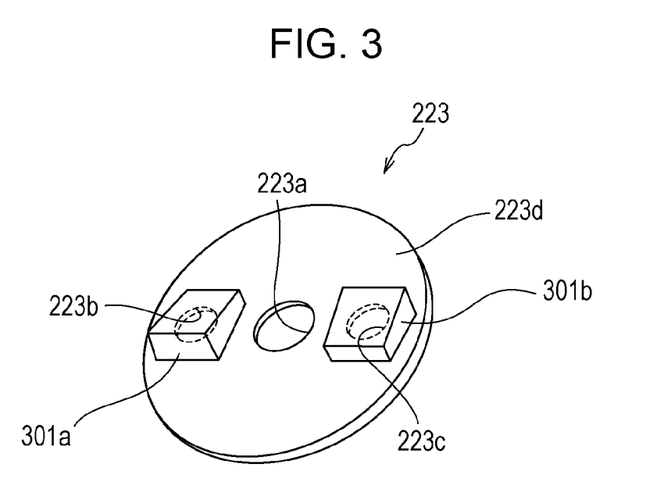
FIG. 3 is a perspective view of an alignment prism diaphragm.

The configuration of the alignment prism diaphragm 223 will now be described with reference to FIG. 3. FIG. 3 is a diagram schematically illustrating the configuration of the alignment prism diaphragm 223. The alignment prism diaphragm 223 includes a disc-shaped aperture plate 223d. Three openings 223a, 223b, and 223c are formed in the aperture plate 223d so as to line up serially. Alignment prisms 301a and 301b which transmit only light beams having wavelengths around 880 nm are attached to the dichroic mirror 212 side of the openings 223b and 223c at either side.

Returning to FIG. 2, anterior ocular segment lighting light sources 221a and 221b are arranged diagonally forward to the anterior ocular segment of the subject eye E. The anterior ocular segment lighting light sources 221a and 221b emit light having wavelength around 780 nm. The anterior ocular segment lighting light sources 221a and 221b project light beams to the anterior ocular segment of the subject eye E. The reflected light beam from the anterior ocular segment of the subject eye E is imaged on the surface of the light-receiving sensor of the imaging device 220 via the dichroic mirror 206, the lens 211, the dichroic mirror 212, and the opening 223a in the center of the alignment prism diaphragm 223. The imaging device 220 converts the optical image of the anterior ocular segment of the imaged subject eye E into electric signals and outputs the electric signals. The system control unit 401 generates an image of the anterior ocular segment of the subject eye E from the electric signals output from the imaging device 220.

The light source for alignment detection is also the eye refraction measuring light source 201.

When performing alignment, a semi-transparent diffusion plate 222 is inserted in the optical path 01 by a diffusion plate insertion and removal solenoid 410 (not illustrated). The diffusion plate 222 is inserted near or at the focus position of the lens 205. As a result, the light beam from the eye refraction measuring light source 201 is projected once on the diffusion plate 222. The projected light then becomes a secondary light source which heads toward the subject eye E from the lens 205 as a thick parallel light beam, and is then projected onto the subject eye E.

This parallel light beam is reflected by a cornea Ef of the subject eye E and forms a bright spot image. A portion of this reflected light beam of the bright spot is reflected by the dichroic mirror 206 again, and then reflected by the dichroic mirror 212 via the lens 211. This reflected light beam passes through the opening 223a in the alignment prism diaphragm 223 and the alignment prisms 301a and 301b, is converged by the imaging lens 218, and is imaged by the imaging device 220.

The opening 223a in the center of the alignment prism diaphragm 223 is configured to pass light beams having wavelengths of at least 780 nm from the anterior ocular segment lighting light sources 221a and 221b. Thus, the light beam illuminated by the anterior ocular segment lighting light sources 221a and 221b and reflected by the anterior ocular segment follows an observation optical path similar to the path of the light beam reflected by the cornea Ef, passing through the opening 223a in the alignment prism diaphragm 223 and being imaged by the imaging device 220 through the imaging lens 218. The imaging device 220 converts the imaged reflected light beam into signals, and outputs the signals.

The light beam which has passed through the alignment prism 301a is refracted upwards, while the light beam which has passed through the alignment prism 301b is refracted downwards (i.e. in the opposite direction).

When performing alignment, the system control unit 401 generates an anterior ocular segment image from the signals which the imaging device 220 outputs. This image includes the bright spot from the light beam which has passed through the alignment prism diaphragm 223. An alignment detecting unit 300 detects the positional relation of the bright spot through the alignment prism 223, from the image which the system control unit 401 has generated, and transmits the detection results to the system control unit 401. The system control unit 401 can perform alignment between the measuring unit 110 and the subject eye E based on the positional relation of the bright spot that has been detected.

System Configuration

Figure 4:
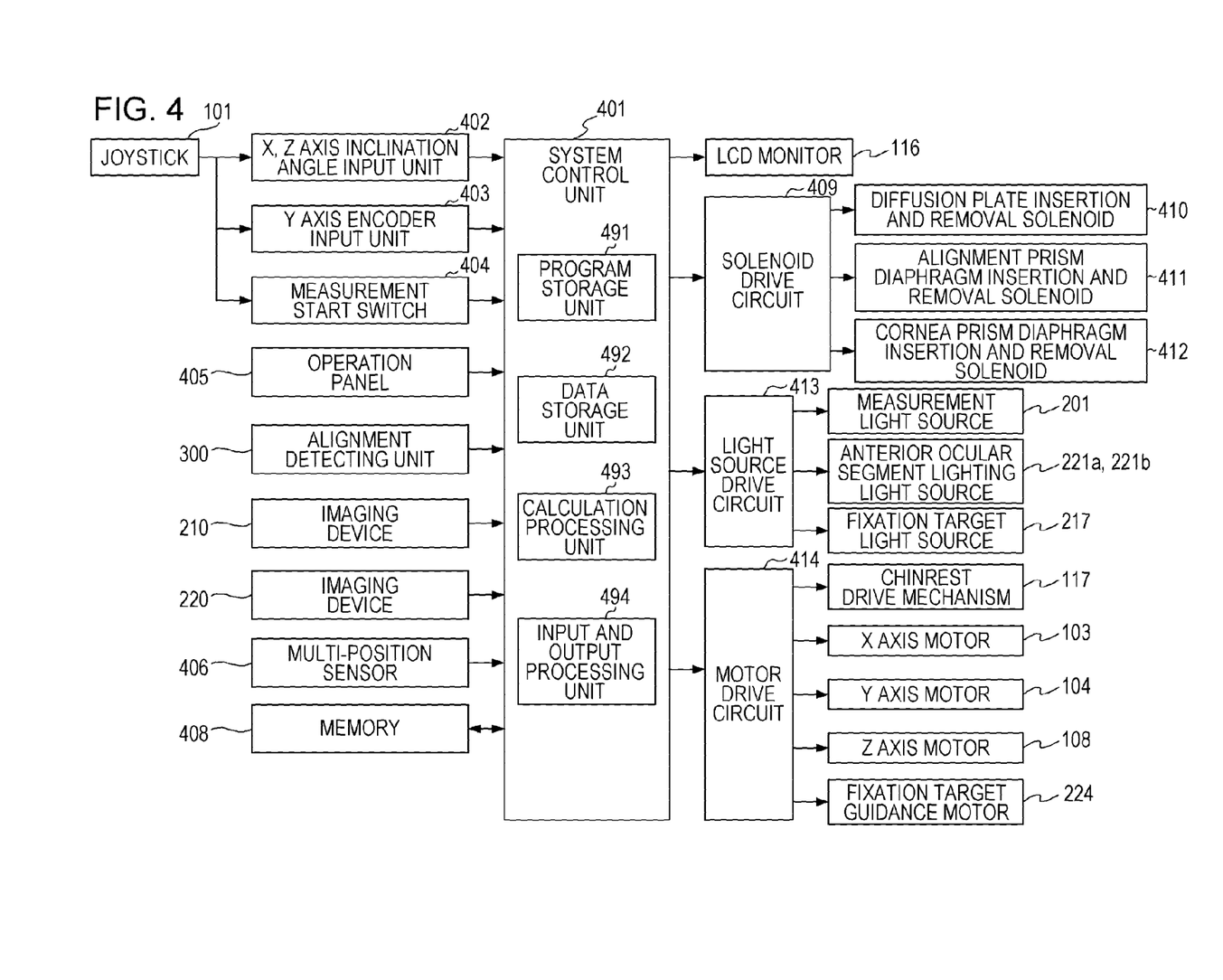
FIG. 4 is a system block diagram of the eye refractometer.

Next, the system configuration of the eye refractometer 1 will be described with reference to the system block diagram in FIG. 4.

The system control unit 401 controls the entire system of the eye refractometer 1. The system control unit 401 also performs predetermined calculation processing. The system control unit 401 includes a program storage unit 491, a data storage unit 492, an input and output processing unit 494, and a calculation processing unit 493. A computer is applied to the system control unit 401. A computer program for controlling the eye refractometer 1 is stored in the program storage unit 491. Data for correcting the eye refraction value, etc. is stored in the data storage unit 492. The input and output control unit 494 controls input and output between various devices. The calculation processing unit 493 processes data obtained from the various devices.

Also, the system control unit 401 functions as an example of an image generating unit which generates images from signals output from the imaging device 210 and imaging device 220, and an image acquisition unit which acquires images which the image generating unit has generated. Note that the image generating unit may be provided externally from the system control unit 401. In this case, the system control unit 401 functions as an example of the image acquisition unit which acquires images generated by the image generating unit. In a configuration where the image generating unit is provided externally from the system control unit 401, the system control unit 401 which is an example of the image acquisition unit is connected to the external image generating unit, either by cable or wirelessly, so as to be able to receive images.

Connected to the system control unit 401 is the joystick 101, via an inclination angle detecting unit 402, encoder input unit 403, and measurement start switch 404. The joystick 101 is an operation member which the examiner operates to position the measuring unit 110 relative to the subject eye E and to start measurement. The inclination angle detecting unit 402 detects forward, backward, left, and right inclination angles when the joystick 101 is operated, and transmits these angles to the system control unit 401. The encoder input unit 403 detects the rotational angle when the joystick 101 is operated, and transmits these angles to the system control unit 401. The measurement start switch 404 transmits signals to the system control unit 401 in response to being operated by the examiner or the like. A print button, chinrest vertical movement buttons, etc. are also disposed on an operation panel 405 on the base 100. When the print button or chinrest vertical movement buttons are operated, signals are transmitted to the system control unit 401 in response to the operations.

Memory 408 stores anterior ocular segment images of the subject eye E imaged by the imaging device 220, ring images for eye refraction calculations imaged by the imaging device 210, and so forth. The system control unit 401 extracts the pupil image Ep of the subject eye E and the cornea reflection image from the images stored in the memory 408, and performs alignment. The system control unit 401 composites text and graphical data into the anterior ocular segment image of the generated subject eye E, and displays on the LCD monitor 116 (shown in FIG. 2). The LCD monitor 116 thus displays the anterior ocular segment image, measurement values, etc.

A solenoid drive circuit 409 drives a diffusion plate insertion and removal solenoid 410, an alignment prism diaphragm insertion and removal solenoid 411 and a cornea prism diaphragm insertion and removal solenoid 412 in accordance with control from the system control unit 401.

A motor drive circuit 414 drives the X-axis drive motor 103, the Y-axis drive motor 104, the Z-axis drive motor 108, the motor in the chinrest drive mechanism 117, and the fixation target guidance motor 224 in accordance with the control from the system control unit 401.

A light source drive circuit 413 turns on/off and changes the amount of light of the eye refraction measuring light source 201, the anterior ocular segment lighting light sources 221a and 221b, and the fixation target lighting light source 217 in accordance with the control from the system control unit 401.

The eye refractometer 1 is also provided with various types of position sensors 406 for detecting the positions of each part. For example, the eye refractometer 1 is provided with position sensors to detect the positions of each of the X-axis drive frame 102, Y-axis drive frame 106, and Z-axis drive frame 107, as position sensors 406. The detection results of each part by the position sensors 406 are transmitted to the system control unit 401.

A computer program for controlling each part is stored in the program storage unit 491 of the system control unit 401. Settings for controlling each part are stored in a computer-readable format in the data storage unit 492 of the system control unit 401. The calculation processing unit 493 of the system control unit 401 reads out a computer program for controlling each part from the program storage unit 491, and executes the program. The calculation processing unit 493 reads out and references settings necessary for control of each part from the data storage unit 492 at this time. Thus, control of each part is realized.

Overall Flow of Operations

Next, the operations of the eye refractometer 1 according to the present embodiment having a configuration such as described above will be described. The operations of the eye refractometer 1 according to the present embodiment include an alignment stage, an anterior ocular segment observation stage, an eye refraction measurement stage which is an example of eye characteristics, and a measurement result determination stage. In the alignment stage, the system control unit 401 positions the measuring unit 110 relative to the subject eye E. In the anterior ocular segment observation stage, the system control unit 401 controls the imaging device 220, the light source drive circuit 413, and the LCD monitor 116 to generate an anterior ocular segment image of the subject eye E and to present the generated anterior ocular segment image. In the eye refraction measurement stage, the system control unit 401 generates a fundus image of the subject eye E, and measures the eye refraction of the subject eye E based on the generated fundus image. In the measurement result determination stage, the system control unit 401 performs determination of whether or not eye refraction measurement was successful, and whether or not the variance in eye refraction measurement values was great (i.e. larger than a predetermined threshold).

In a case where eye refraction measurement was not successful, or in a case where variance in eye refraction measurement values was great, a subsequent transillumination stage ensues. In the transillumination stage, the system control unit 401 generates a transillumination moving image of the subject eye based on signals output from the imaging device 220. The system control unit 401 then performs transillumination observation, and determines whether or not the subject eye E is an IOL eye, using the generated transillumination image. In a case where determination is made that the subject eye E is an IOL eye, a subsequent eye refraction re-measurement stage ensues. In the eye refraction re-measurement stage, the system control unit 401 changes the various settings for measurement to settings suitable of a subject eye E which is an IOL eye, and performs measurement with these.

Alignment

Figure 5:
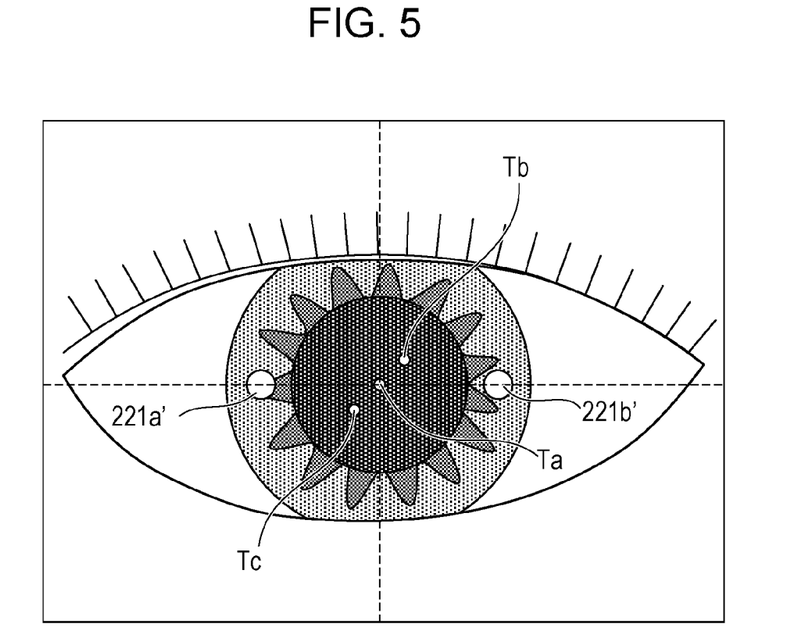
FIG. 5 is an explanatory diagram of the anterior ocular segment image.

Now, alignment operations will be described with reference to FIG. 5. FIG. 5 is a diagram schematically illustrating an anterior ocular segment image of the subject eye E generated from signals output by the imaging device 220.

When performing alignment, the light beam of the eye refraction measuring light source 201 also used as an alignment light source is imaged by the cornea Ef and becomes a cornea bright spot. The cornea bright spot (light beam from the cornea Ef) is divided between the openings 223a, 223b, and 223c of the alignment prism diaphragm 223, and the alignment prisms 301a and 301b (see FIG. 3). Cornea bright spots obtained by the dividing are included in the anterior ocular segment image generated from signals output by the imaging device 220. These cornea bright spots Ta, Tb, and Tc serve as index images. The subject eye E illuminated by the anterior ocular segment lighting light sources 221a and 221b gives rise to bright spot images 221a' and 221b' of the anterior ocular segment lighting light sources 221a and 221b.

The alignment detecting unit 300 detects the three cornea bright spots (index images) Ta, Tb, and Tc from the generated anterior ocular segment image. The alignment detecting unit 300 then transmits the detection results of the three detected cornea bright spots Ta, Tb, and Tc to the system control unit 401. The system control unit 401 moves the measuring unit 110 horizontally and vertically so that the center cornea bright spot Ta is situated at the center of the anterior ocular segment image. After the center cornea bright spot Ta is situated at the center of the image, the system control unit 401 further moves the measuring unit 110 back and forth so that the cornea bright spots Tb and Tc are vertically aligned with the cornea bright spot Ta. Once a state is achieved where the three cornea bright spots (index images) Ta, Tb, and Tc are aligned in one row in the vertical direction, the alignment is complete.

Note that movement of the measuring unit 110 is performed by the system control unit 401 controlling the motor drive circuit 414, and the motor drive circuit 414 driving each of the motors under control of the system control unit 401.

Measurement of Eye Refraction

Next, the operations to measure the eye refraction will be described.

First, the system control unit 401 removes, from the optical path 01, the diffusion plate 222 previously inserted into the optical path 01 for auto-alignment. The system control unit 401 controls the light source drive circuit 413, so that the light source drive circuit 413 adjusts the amount of light from the eye refraction measuring light source 201 under control of the system control unit 401. Thus, the measurement light beam emitted by the eye refraction measuring light source 201 is projected to the fundus Er of the subject eye E.

The reflected light from the fundus Er of the subject eye E follows the optical path 02 and is imaged on the imaging device 210. The system control unit 401 generates a fundus image from the signals output from the imaging device 210. The system control unit 401 generates a fundus image from the signals output from the imaging device 210. The generated fundus image has a ring image corresponding to the refraction of the subject eye E caused by the ring diaphragm 207. The system control unit 401 stores this ring image in the memory 408.

The system control unit 401 calculates the center of gravity coordinates for the ring image stored in the memory 408, and obtains equation for the ellipse by a known method. The system control unit 401 calculates the major axis, minor axis, and inclination of the major axis for the obtained ellipse, and then calculates the eye refraction value of the subject eye E further based on this. This eye refraction calculation method may also use a known calculation method.

The system control unit 401 references the obtained eye refraction value, moves the lens 215 to the position corresponding to this eye refraction value, and presents the fixation target 216 to the subject eye E at the refractive index corresponding to the refractive index of the subject eye E. This operation is executed by the system control unit 401 controlling the motor drive circuit 414 and the motor drive circuit 414 driving the fixation target guidance motor 224. Afterwards, the system control unit 401 moves the lens 215 away for a predetermined distance, fogs the fixation target 216, and in that state lights the eye refraction measuring light source 201 again to measure the eye refraction of the subject eye E.

In this way, the system control unit 401 measures the eye refraction of the subject eye E, fogs the fixation target 216, and performs measurement of the eye refraction, and repeats this operation. As a result, the system control unit 401 can obtain a stable final measurement value of the eye refraction of the subject eye E.

Transillumination Observation

Normally, the above-described operation ends measurement of eye refraction. However, if the variance of refraction values obtained from eye refraction is great, or measurement of eye refraction itself was unsuccessful, there is the possibility that there is a disorder of the eye such as cataracts, or the subject eye E is an IOL eye.

Accordingly, the system control unit 401 determines whether or not eye refraction was successfully measured after the above-described eye refraction measurement operation ends, and in a case where determination is made that eye refraction was successfully measured, determines whether or not variance of measurement values is at or greater than a threshold value. Note that the threshold value of the variance of measurement values is not restricted in particular, and is set as appropriate based on past results and so forth. In a case where the variance of measurement values obtained from eye refraction is greater than a predetermined threshold, or measurement of eye refraction itself was unsuccessful, the system control unit 401 performs transillumination observation (observation of the subject eye E by transillumination), and identifies the cause.

Transillumination observation is a method to observe opacity of the subject eye E. In transillumination observation, light is cast into the subject eye E, and an image of reflected light from the fundus Er is generated. In a case where the crystalline lens of the subject eye E has no opacity, the pupil Ep in the generated image is uniformly bright. In a case where the crystalline lens of the subject eye E has opacity due to cataracts, the light beam cast from the eye refraction measuring light source 201 does not reach the fundus Er due to the opacity. Accordingly, the imaging device 210 cannot detect reflected light, and measurement cannot be performed.

The system control unit 401 then identifies the cause by transillumination observation, and in a case where the crystalline lens of the subject eye E has opacity, performs transillumination refractive measurement. Transillumination refractive measurement is refractive measurement performed from the transillumination image at a portion avoiding the opacity of cataracts. Even if the subject eye E has cataracts, transillumination refractive measurement enables measurement of eye refraction.

On the other hand, in a case where the subject eye E is an IOL eye or the like, the shape of the IOL, material, whether or not refraction adjustment capabilities are possessed, and so forth, are characteristics different from those of the crystalline lens. Accordingly, once determination can be made that the subject eye E is an IOL eye, precise measurement matching these characteristics can be performed.

On the other hand, variance in measurement values is great with a diffractive multifocal IOL since refraction differs depending on the position. Accordingly, the system control unit 401 automatically determines whether or not the IOL is a monofocal IOL or a diffractive multifocal intraocular lens. Thus, refraction error can be reduced, and accurate measurement can be made in accordance with the type of the IOL.

Figure 6A:
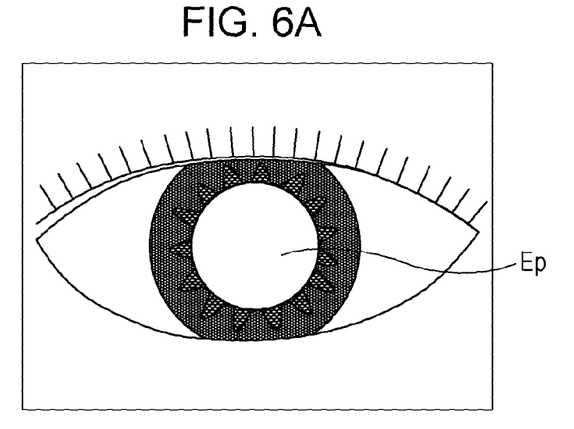
FIGS. 6A through 6C are explanatory diagrams of transillumination observation.

FIG. 6A is a diagram illustrating an example of a transillumination image of a non-IOL eye. If the subject eye E has cataracts, no image may be obtained due to opacity, or a shadow (not illustrated) may show up in the pupil Ep.

Figure 6B:
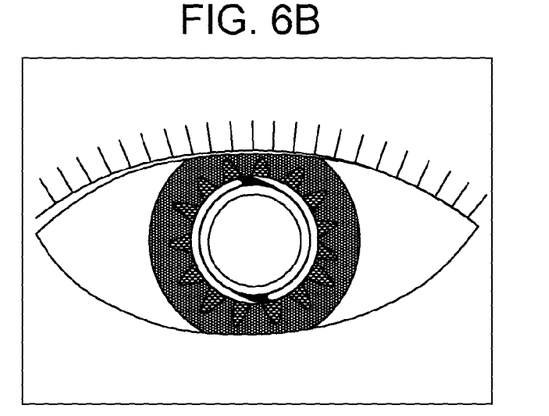

FIG. 6B is a diagram illustrating an example of a transillumination image of an IOL eye. The transillumination image of an IOL eye exhibits an edge of the anterior capsule formed by ocular lens insertion surgery (interface between capsule and ocular lens), and the edge of the IOL.

Figure 6C:
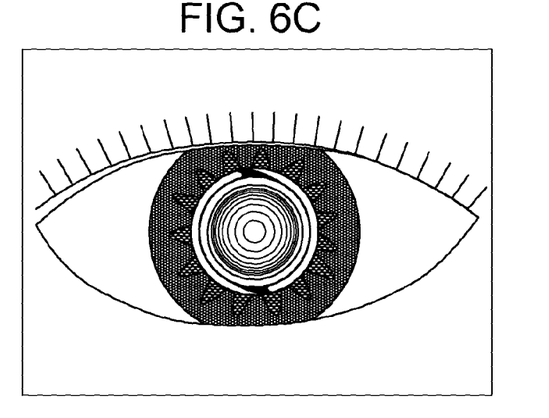

FIG. 6C is a diagram illustrating an example of a transillumination image of a diffractive multifocal IOL eye. The transillumination image of a diffractive multifocal IOL eye exhibits, in addition to the edge of the anterior capsule and the edge of the IOL in the same way as with FIG. 6B, multiple concentric rings (interference pattern) due to the diffractive multifocal IOL.

IOL Eye Determination Processing

Figure 7:
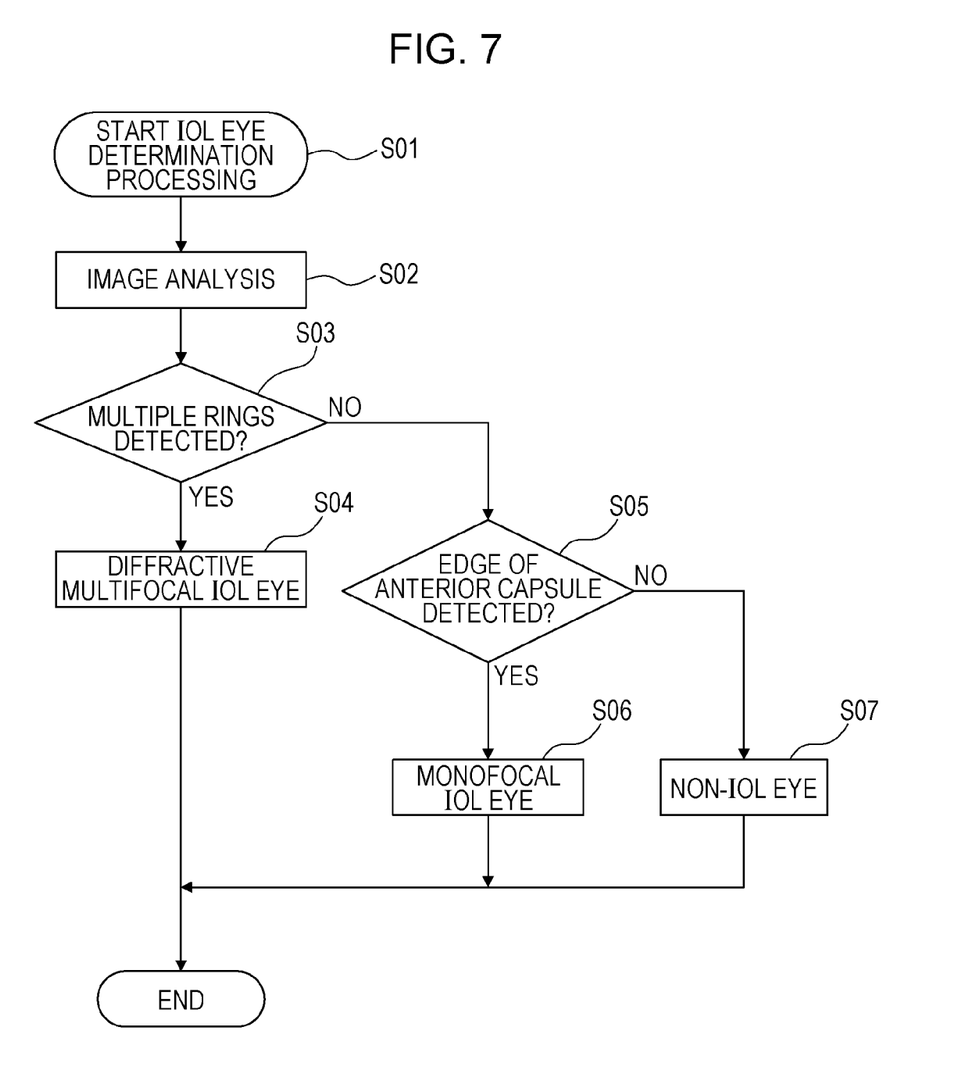
FIG. 7 is a flowchart illustrating IOL eye determination processing.

Next, the IOL eye determination processing to determine whether or not the subject eye E is an IOL eye will be described with reference to FIGS. 7 through 8C. FIG. 7 is a flowchart illustrating IOL eye determination processing in transillumination refraction measurement. FIGS. 8A through 8C are schematic diagrams illustrating examples of transillumination images used in IOL eye determination processing. A computer program for executing this processing is stored in the program storage unit 491 of the system control unit 401 beforehand. The calculation processing unit 493 of the system control unit 401 reads out this computer program from the program storage unit 491, and executes the program. Thus, the following processing is realized.

In step S01, the system control unit 401 starts the IOL eye determination processing. We will say that when starting the IOL eye determination processing, the measuring unit 110 is at a position where transillumination images can be observed. Also, we will say that the system control unit 401 has generated and acquired a transillumination image of the subject eye E from signals which the imaging device 220 outputs.

In step S02, the system control unit 401 which is an example of an analyzing unit performs analysis of luminance distribution on a straight line passing through the center of the subject eye E in the generated transillumination image (hereinafter, this straight line will be referred to as "analysis axis" AA). As indicated by the arrow in FIG. 8A for example, the system control unit 401 analyzes the luminance distribution following a vertical axis as the analysis axis. Note that FIG. 8A illustrates an example of a non-IOL eye transillumination image and luminance distribution, FIG. 8B illustrates an example of a monofocal IOL eye transillumination image and luminance distribution, and FIG. 8C illustrates an example of a diffractive multifocal IOL eye transillumination image and luminance distribution. The luminance distributions are illustrated in FIGS. 8A through 8C in accordance with a case where the luminance gradation is 256 levels. If there is no mydriatis, the edge of the IOL will often not be visible and a surgical scar on the anterior capsule will often appear above.

Figure 8A:
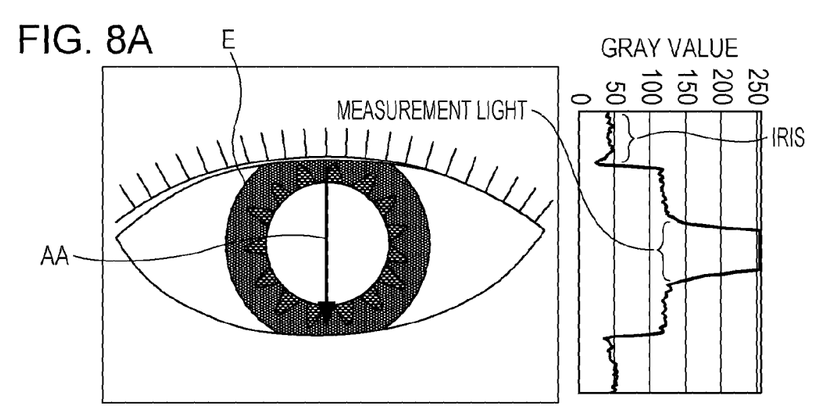
FIGS. 8A through 8C are schematic diagrams illustrating an example of image analysis.

As illustrated in the luminance distribution in FIG. 8A, luminance is locally low at the iris portion in a non-IOL eye. Also, the luminance of the center portion is higher than the other portions due to effects of the illumination light, but when these two are excluded, the luminance is uniform.

Figure 8B:
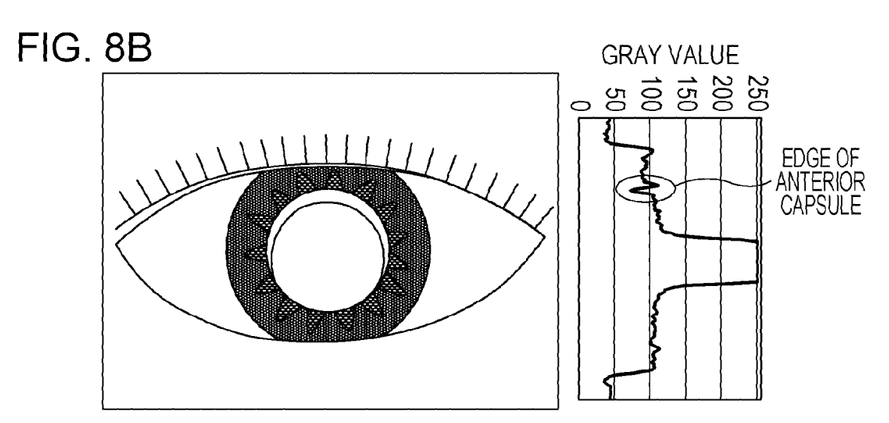

As illustrated in the luminance distribution in FIG. 8B, luminance of a monofocal IOL eye is the same as with a non-IOL eye (FIG. 8A) at the iris portion and center portion. In the pupil Ep, there is a portion where the luminance level is locally lower than other portions by almost 50. In a case where the locally low luminance is present on the entire perimeter, this means that the portion with low luminance is formed in a ring shape. However, only information from one direction (vertical direction) yields only understanding that there is a locally dark part. Accordingly, the system control unit 401 rotates the analysis axis on the center of the subject eye E, and analyzes the luminance distribution for the entire perimeter at predetermined angle stops. The system control unit 401 then determines whether or not the luminance level includes a locally low portion in a ring shape. In a case where the luminance level does include a locally low portion in a ring shape, this portion with locally low luminance can be determined to be the edge of the anterior capsule.

Figure 8C:
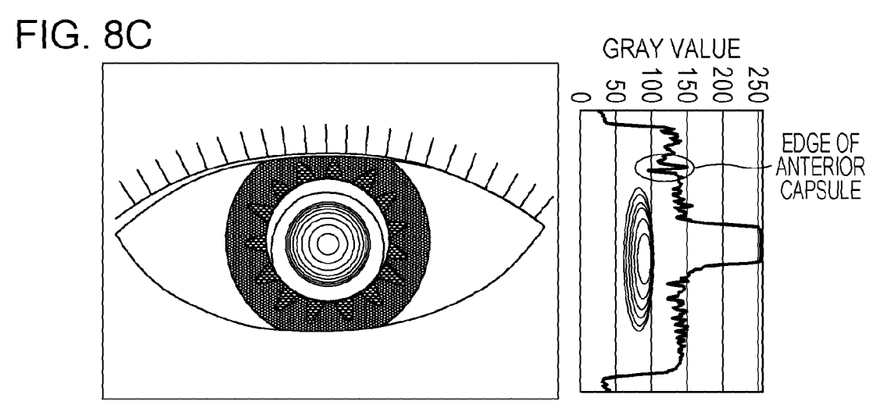

As illustrated in the luminance distribution in FIG. 8C, luminance of a diffractive multifocal IOL eye is the same as with a monofocal IOL eye (FIG. 8B) in that there is a portion where the luminance level is locally lower. Further, there is a tendency for the luminance in the pupil Ep to change in level by 10 or more at a predetermined cycle. This is due to a diffractive multifocal IOL. Accordingly, the system control unit 401 rotates the analysis axis on the center of the subject eye E, and analyzes the luminance distribution at predetermined angle stops. The system control unit 401 then determines whether or not the luminance level includes locally low portions exist on the entire perimeter. In a case where the luminance level does include locally low portions on the entire perimeter, this can be determined as being multiple concentric rings such as illustrated in FIG. 8C. The example illustrated in FIGS. 8A, 8B and 8C use a gray value (in a grayscale of 0 to 256) to illustrate the variation in luminance. However, another scale may be understood by the skilled person to be useable here.

By performing such analysis, the system control unit 401 can detect characteristics different from those of a non-IOL eye, and thus detect IOL eyes.

In step S03, the system control unit 401 determines whether multiple concentric rings have been detected. In a case where multiple concentric rings have been detected such as illustrated in FIG. 8C, the flow advances to step S04. Otherwise, the flow advances to step S05.

In step S04, the system control unit 401 which is an example of a determining unit determines that the subject eye E is a diffractive multifocal IOL eye. The system control unit 401 (display control unit) then displays determination results to the effect that the subject eye E is a diffractive multifocal IOL eye, on the LCD monitor 116 which is an example of a display unit.

In step S05, the system control unit 401 performs detection of the edge of the anterior capsule. In a case where the edge of the anterior capsule of the subject eye E has been detected from a luminance distribution such as illustrated in FIG. 8B, the flow advances to step S06. Otherwise, the flow advances to step S07.

In step S06, the system control unit 401 which is an example of a determining unit determines that the subject eye E is a monofocal IOL eye. The system control unit 401 (display control unit) then displays determination results to the effect that the subject eye E is a monofocal IOL eye, on the LCD monitor 116.

In step S07 (case where no anterior capsule edge was detected in step S04), the system control unit 401 which is an example of a determining unit determines that the subject eye E is a non-IOL eye. The system control unit 401 (display control unit) then displays determination results to the effect that the subject eye E is a non-IOL eye, on the LCD monitor 116.

By following the above flow, whether or not the subject eye is an IOL eye can be determined. This flow enables whether or not an IOL eye to be determined automatically, without adding any special equipment (equipment not directly related to the measurement).

Re-Measurement of Eye Refraction

In a case where the subject eye E has been determined to be a diffractive multifocal IOL eye or a monofocal IOL eye, the system control unit 401 changes the measurement conditions of eye refraction, which is an example of eye characteristics. For example, the system control unit 401 changes the light quantity of the fixation target, the focusing method, or the major axis calculation method for the subject eye E, to a light quantity or method suitable for an IOL eye.

The system control unit 401 then performs eye fraction measurement again using the changed measurement conditions (light quantity or method). Note that settings suitable for non-IOL eyes, settings suitable for monofocal IOL eyes, and settings suitable for diffractive multifocal IOL eyes are stored in the data storage unit 492 of the system control unit 401 beforehand in a computer-readable format. The calculation processing unit 493 reads out and uses these settings in accordance with the results of the IOL eye determination processing when performing eye refraction measurement. Items to be set and specific setting values are not restricted in particular, and may be set as appropriate based on past results or the like, for example.

Measurement conditions to be changed in a case of the subject eye E having been determined to be an IOL eye, and the contents of change, are as follows, for example.

(1) The system control unit 401 makes a display on the LCD monitor 109 to the effect that the subject eye E is a refractive multifocal IOL eye or monofocal IOL eye.

(2) The system control unit 401 alleviates error conditions for measurement.

(3) The system control unit 401 omits the sequence to fog the fixation target 216.

(4) The system control unit 401 darkens the fixation target 216 to prevent contracting of the pupil of the subject eye E. That is to say, the system control unit 401 reduces the amount of light of the fixation target lighting light source 217 projecting the fixation target 216 to a level lower than for a case where the subject eye E is not an IOL eye.

Note that these conditions do not all have to be changed and that the conditions may be changed selectivity.

In a case where the ophthalmic device is a fundus camera, the driving control is changed so as to reduce flaring when photographing.

Also, in a case where the ophthalmic device is an axial length measurement device, measurement values corresponding to the state of the subject eye E can be obtained.

As described above, according to the embodiment of the present invention, whether or not a subject eye E is an IOL eye can be automatically determined. Accordingly, there is no concern that the examination may end in failure due to misunderstanding or erroneous operations of the examiner. Also, the examiner does not have to input information regarding whether or not the subject eye E is an IOL eye. Accordingly, the burden on the examiner is alleviated, and the examination time is reduced. Further, the IOL eye determination processing is performed by the system control unit 401 based on image analysis. Accordingly, no special hardware is necessary to determine whether or not the subject eye E is an IOL eye, so this arrangement avoids increased scale and complexity of the device.

While an embodiment of the present invention has been described in detail, the embodiment only serves as a specific example to illustrate an implementation of the present invention. The technical scope of the present invention is not limited to the embodiment. Various modifications may be made to the present invention without departing from the scope of the present invention, and these are included in the technical scope of the present invention.

For example, regarding the embodiment, an eye refractometer has been illustrated as an example of the ophthalmic device, but the ophthalmic device is not restricted to an eye refractometer. Regarding the present invention, ophthalmic measuring devices other than an eye refraction measuring device such as an ophthalmic photographing device, an ocular axial length measuring device, optical coherence tomography (OCT), etc., are applicable to the IOL eye determination according to the present invention, as long as the device is capable of transillumination observation.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-086879, filed Apr. 17, 2013, which is hereby incorporated by reference herein in its entirety.

What is claimed is:

1. An ophthalmic device comprising:
   an acquisition unit configured to acquire a transillumination image of a pupil of a subject eye; and
   a determining unit configured to determine whether or not the subject eye includes an intraocular lens, based on the acquired transillumination image.

2. The ophthalmic device according to claim 1, further comprising:
   a projecting unit configured to project a light beam to the fundus of the subject eye;
   wherein the acquisition unit acquires a transillumination image of the pupil illuminated by a reflected light beam from the fundus.

3. The ophthalmic device according to claim 1, further comprising:
   an analyzing unit configured to analyze luminance distribution of the transillumination image acquired by the acquisition unit;
   wherein the determining unit determines whether or not the subject eye includes an intraocular lens, based on the analyzed luminance distribution.

4. The ophthalmic device according to claim 3,
   wherein the determining unit detects, from the luminance distribution analyzed by the analyzing unit, whether or not there exists a ring-shaped portion of low luminance, and in a case where the ring-shaped portion of low luminance exists, determines the subject eye to include the intraocular lens.

5. The ophthalmic device according to claim 4,
   wherein the determining unit detects a ring-shaped portion of low luminance caused by an interface between a capsule of the subject eye and the intraocular lens or by an edge of the intraocular lens.

6. The ophthalmic device according to claim 3, wherein the determining unit detects, from the luminance distribution analyzed by the analyzing unit, whether or not there exist multiple concentric rings of low luminance and, in a case where the multiple concentric rings exist, determines the subject eye to include a diffractive multifocal intraocular lens.

7. The ophthalmic device according to claim 3, wherein the determining unit determines whether or not a portion which is locally low in luminance exists, using distribution of luminance on a straight line passing through the center of the subject eye as the luminance distribution, and also analyzes the luminance distribution on the entire perimeter of the subject eye, thereby determining whether the portion of low luminance forms a ring shape.

8. The ophthalmic device according to claim 3, further comprising:
a display control unit configured to display determination results from the determining unit on a display unit.

9. The ophthalmic device according to claim 1, further comprising:
a measuring unit configured to measure eye characteristics of the subject eye;
wherein, in a case where the subject eye has been determined by the determining unit to have an intraocular lens, the measuring unit changes measurement conditions of the eye characteristics of the subject eye.

10. The ophthalmic device according to claim 9, wherein, in a case of measuring eye refraction of the subject eye as the eye characteristics of the subject eye, the measuring unit performs at least one of
omitting fogging of a fixation target, and
reducing a light quantity from a light source projecting the fixation target to the subject eye so as to be less than that of a case where the subject eye does not have the intraocular lens,
as the change to the measurement conditions.

11. A control method of an ophthalmic device, the method comprising:
acquiring a transillumination image of a pupil of a subject eye; and
determining whether or not the subject eye includes an intraocular lens, based on the acquired transillumination image.

12. The control method of an ophthalmic device according to claim 11, further comprising:
projecting a light beam to the fundus of the subject eye, and acquiring a transillumination image of the pupil illuminated by a reflected light beam from the fundus.

13. The control method of an ophthalmic device according to claim 11, further comprising:
analyzing luminance distribution of the transillumination image acquired by the acquisition unit, and determining whether or not the subject eye includes an intraocular lens, based on the analyzed luminance distribution.

14. The control method of an ophthalmic device according to claim 13, further comprising:
detecting whether or not there exists a ring-shaped portion of low luminance from the analyzed luminance distribution, and, in a case where the ring-shaped portion of low luminance exists, determining the subject eye to include the intraocular lens.

15. The control method of an ophthalmic device according to claim 14, wherein the detecting further includes
detecting whether or not there exists a ring-shaped portion of low luminance which is generated by an interface between a capsule of the subject eye and the intraocular lens or an edge of the intraocular lens from the analyzed luminance distribution.

16. The control method of an ophthalmic device according to claim 13, further comprising:
determining whether or not there exist multiple concentric rings of low luminance due to a diffractive multifocal intraocular lens from the analyzed luminance distribution, and in a case where the multiple concentric rings exist, the intraocular lens is determined to be a diffractive multifocal intraocular lens.

17. The control method of an ophthalmic device according to claim 13, further comprising:
determining whether or not a portion which is locally low in luminance exists using distribution luminance on a straight line passing through the center of the subject eye as the luminance distribution, and analyzing the luminance distribution on the entire perimeter of the subject eye, thereby determining whether the portion of low luminance forms a ring shape.

18. The control method of an ophthalmic device according to claim 13, further comprising:
displaying determination results regarding whether or not the subject eye includes an intraocular lens.

19. The control method of an ophthalmic device according to claim 11, further comprising:
measuring eye characteristics of the subject eye;
wherein, in a case where the subject eye has been determined to have an intraocular lens, the measuring unit changes the measurement conditions of the eye characteristics in the measuring of eye characteristics of the subject eye.

20. The control method of an ophthalmic device according to claim 19, further comprising:
in a case of measuring eye refraction of the subject eye as the eye characteristics, performing at least one of
omitting fogging of a fixation target, and
reducing the light quantity from a light source projecting the fixation target to the subject eye so as to be less than that of a case where the subject eye does not have the intraocular lens,
as a change to the measurement conditions.

21. A non-transitory tangible medium storing a program to cause a computer to execute the control method of an ophthalmic device according to claim 11.

* * * * *